United States Patent
Rittri (10) Patent No.: US 11,884,557 B2
(45) Date of Patent: Jan. 30, 2024

(54) CONTAINER WITH UV PURIFICATION

(71) Applicant: Bluewater Sweden AB, Stockholm (SE)

(72) Inventor: Bengt Rittri, Stockholm (SE)

(73) Assignee: BLUEWATER SWEDEN AB, Stockholm (SE)

( * ) Notice: Subject to any disclaimer, the term of this patent is extended or adjusted under 35 U.S.C. 154(b) by 9 days.

(21) Appl. No.: 17/545,176

(22) Filed: Dec. 8, 2021

(65) Prior Publication Data

US 2022/0185705 A1 Jun. 16, 2022

(30) Foreign Application Priority Data

Dec. 15, 2020 (SE) .................................... 2051467-5

(51) Int. Cl.
*C02F 1/32* (2023.01)
*C03C 17/23* (2006.01)

(52) U.S. Cl.
CPC .............. *C02F 1/325* (2013.01); *C03C 17/23* (2013.01); *C02F 2201/002* (2013.01); *C02F 2201/32* (2013.01); *C02F 2303/04* (2013.01); *C02F 2305/10* (2013.01); *C03C 2217/212* (2013.01); *C03C 2217/71* (2013.01)

(58) Field of Classification Search
CPC ...... C02F 1/32; C02F 1/72; C02F 1/78; C02F 1/48; C02F 1/46; B01D 32/34; B01D 61/10; B01D 61/08; A61L 2/10
See application file for complete search history.

(56) References Cited

U.S. PATENT DOCUMENTS 6,447,721 B1* 9/2002 Horton, III ............... A61L 2/10
                                                      210/748.11
9,566,358 B1 2/2017 Koh et al.
(Continued)

FOREIGN PATENT DOCUMENTS

CN 109095549 A 12/2018
EP 2829518 A1 1/2015
(Continued)

OTHER PUBLICATIONS

Swedish Search Report from corresponding Swedish Application 2051467-5, dated Jul. 23, 2021, 7 pages.
(Continued)

*Primary Examiner* — Walter D. Griffin
*Assistant Examiner* — Cameron J Allen
(74) *Attorney, Agent, or Firm* — Ronald M. Kachmarik; Cooper Legal Group LLC (57) ABSTRACT

A water container for purifying water. The water container includes an opening configured to receive water, a container body arranged to enclose the water and a water purifying unit configured to purify the water. The water purifying unit includes an at least partially transparent plate, which includes a coating of metal-oxide nanoparticles on a first side facing the container body, wherein the first side is configured to be in contact with the water, and an ultraviolet light module configured to radiate towards a second side of the at least partially transparent plate such that light from the ultraviolet light module at least partially passes through the at least partially transparent plate. Also, a method for purifying water within a water container.

14 Claims, 4 Drawing Sheets

(56) References Cited

U.S. PATENT DOCUMENTS

| | | | |
|---|---|---|---|
| 10,570,028 B2 | 2/2020 | Liao et al. | |
| 2016/0107904 A1* | 4/2016 | Rajagopalan | C02F 1/325 |
| | | | 250/432 R |
| 2016/0289090 A1* | 10/2016 | Liao | A23L 3/28 |
| 2017/0190598 A1 | 7/2017 | Liao et al. | |
| 2018/0194645 A1 | 7/2018 | Hsu et al. | |

FOREIGN PATENT DOCUMENTS

| | | |
|---|---|---|
| IT | 20120085 A1 | 2/2014 |
| JP | 2002052386 A | 2/2002 |
| JP | 2004195461 A | 7/2004 |
| KR | 20130106992 A | 10/2013 |
| WO | 2016022817 A1 | 2/2016 |
| WO | 2018232303 A1 | 12/2018 |

OTHER PUBLICATIONS

Extended European Search Report from corresponding European Application No. 21211989.5 dated May 13, 2022.

\* cited by examiner

CONTAINER WITH UV PURIFICATION

TECHNICAL FIELD

The present disclosure relates generally to the technical field of water purification systems and, more particularly, to water purification systems inside water containers.

BACKGROUND

Water purification is a large field and there are many different solutions to purify water. One approach is through the photocatalytic capabilities of metal-oxide nanomaterials. When certain engineered metal-oxide nanomaterials are exposed to ultraviolet radiation while in contact with water they can produce radicals that may be harmful to pollutant organisms in the water, for example bacteria. One example of a metal-oxide with these properties is Titanium Dioxide, $TiO_2$, that has further been seen in prior art to aid in the decomposition of cyanide in water. Photocatalysis can also be used to decompose pollutants in air to enhance its quality or on surfaces of objects. In prior art large areas of $TiO_2$ are used to achieve a good photocatalytic effect and pure water.

Solutions presented in prior art involve coating the insides of water containers with metal-oxides to provide a photocatalytic effect to purify the water with the use of sunlight shining on the sides of the container initializing the photocatalytic effect.

There is a need in the art for new and more available water purification system that does not rely on sunlight being available.

SUMMARY

The inventor has reached the insight that the purifying properties of the photocatalytic effect from metal-oxides and that of ultraviolet light can be combined using a at least partially transparent plate. The inventor has further reached the insight that such a constellation can be easily fitted into smaller containers, such as water bottles or the like, ensuring a low-cost solution for small confined spaces.

In prior art there are many potential photocatalysts, one of the most promising and widespread substances is nanoparticles of $TiO_2$. Nanosized particles may be preferred to larger pieces of $TiO_2$ because of the reactivity, nanoparticles will have a larger combined surface area that can react with the ultraviolet light. $TiO_2$ is chemically stable and has a high ability of breaking molecular bonds, which leads to degradation. $TiO_2$ is further rather inexpensive due to its abundancy.

$TiO_2$ can act as photocatalyst due to it being a semiconductor. $TiO_2$ can come in different states, for example as nanosized or nanoparticles of anatase $TiO_2$ which does not absorb any visible light. However, it strongly absorbs ultraviolet light which leads to the formation of hydroxyl radicals. This occurs when photo-induced valence bond holes ($h^+_{vb}$) are trapped at the surface of $TiO_2$ leading to the formation of trapped holes ($h^+_{tr}$) that cannot oxidize water, the following is an example of a reaction that can take place:

$$TiO_2 + hv \rightarrow e^{31} + h^+_{vb}$$

$$h^+_{vb} \rightarrow h^+_{tr}$$

$$O_2 + e^{31} \rightarrow O_2^{\cdot-}$$

$$O_2^{\cdot-} + O_2^{\cdot-} + 2H^+ \rightarrow H_2O_2 + O_2$$

$$O_2^{\cdot-} + h^+_{vb} \rightarrow O_2$$

$$O_2^{\cdot-} + h^+_{tr} \rightarrow O_2$$

$$OH^- + h^+_{vb} \rightarrow HO\cdot$$

In this reaction the wavelength $(\lambda) = 387$ nm. The above reaction has been found to mineralize and decompose undesirable compounds in the environment where it takes place, specifically in air and in wastewater.

Ultraviolet, UV, light comes in different frequencies, i.e. different energies. A usual classification system is UVA, UVB, and UVC light where UVC has the highest energy. UVB is usually what causes suntans whereas UVC from the sun is blocked and absorbed entirely by the atmosphere. Using UV-light to cleanse air and liquids is well known in the prior art available.

The present disclosure seeks to provide at least some embodiments of a water container which overcome at least some of the above mentioned drawbacks. More specifically, the present disclosure aims at providing at least some embodiments offering a water container for purifying water through a combination of both UV light and the photocatalytic effect from metal-oxides by using an at least partially transparent plate coated with nanoparticles of the metal-oxides.

In a first aspect of the present disclosure there is provided a water container for purifying water. The water container comprises an opening configured to receive water, and a container body arranged to enclose the water. The water container further comprises a water purifying unit configured to purify the water. The water purifying unit comprises an at least partially transparent plate comprising a coating of metal-oxide nanoparticles on a first side facing the container body. The first side is configured to be in contact with the water. The water purifying unit further comprises an ultraviolet light module configured to radiate towards a second side of the at least partially transparent plate such that light from the ultraviolet light module at least partially passes through the at least partially transparent plate.

In a second aspect of the present disclosure there is provided a method for purifying water within a water container. The method comprises filling a container body of the water container with water through an opening, radiating ultraviolet light from a first end of the water container towards a second end of the water container. The method further comprises transmitting at least part of the ultraviolet light through an at least partially transparent plate towards the container body, wherein the at least partially transparent plate comprises a coating of metal-oxide nanoparticles on a first side facing the container. The method further comprises illuminating the container body with the ultraviolet light.

Thus, there is provided a container and a method with a first function of purifying water with the use of ultraviolet light. Further, there is also provided the function of purifying water with the use of the photocatalytic effect of the metal-oxide nanoparticles when illuminated with ultraviolet light. The present device and method have many benefits. For example, allowing for a small and convenient water container that can be brought along by a user for purifying water when there is no large water purification system available. It is also advantageous to combine the method of purifying water using ultraviolet light and using the photocatalytic effect to ensure that the water is drinkable.

According to an embodiment the coating of metal-oxide nanoparticles comprises Titanium Dioxide, $TiO_2$. The present embodiment is advantageous in that $TiO_2$ has a proven effect of cleaning water when illuminated with ultraviolet light and ensures that the water is drinkable. It is further advantageous in that $TiO_2$ is abundant and readily available to use which ensures a low cost and functioning product. The coating of metal-oxide nanoparticles may be placed along the edges of the at least partially transparent plate leaving an uncovered area where UV-light can pass through the at least partially transparent plate. The coating may also be evenly distributed on the whole at least partially transparent plate.

According to another embodiment the at least partially transparent plate is a glass plate. The present embodiment is advantageous in that glass is transparent and easily available. It is however understood that other transparent or at least partially transparent materials can be used, for example different plastics.

According to another embodiment the ultraviolet light module is configured to radiate UVC light. The present embodiment is advantageous in that UVC light has a higher frequency and therefore a higher energy content which makes it more suitable for purifying substances such as water. When light interacts with pollutants in water it is beneficial if the light has a high energy to ensure that the pollutants are neutralized. Further, UVC light will when interacting with the metal-oxide nanoparticles of the coating of the at least partially transparent plate be absorbed and cause the photocatalytic effect which will purify the water.

According to another embodiment the at least partially transparent plate is slidably arranged inside the water container. The present embodiment is advantageous in that a user can adjust the position of the at least partially transparent plate after filling or removing water from it. This may be advantageous in that the at least partially transparent place always may be placed in a position so that the first side comprising the metal-oxide nanoparticles is in contact with the water inside the container to achieve the photocatalytic effect. Other approaches are of course available to a person skilled in the art, for example by placing the at least partially transparent plate in a bottom portion of the water container letting the water rest upon the plate. Or by placing the at least partially transparent plate in a lid element of the water container and when purifying turning the water container upside down allowing water to come into contact with the plate.

According to another embodiment the water container further comprises a lid element, wherein said water purifying unit is arranged inside said lid element. The present embodiment is advantageous in that the design of the water container can be made compact. It is further advantageous in that the water purifying unit can be reached easily for maintenance of for example the ultraviolet light module. The lid element may for example have a flat upper surface allowing the water container to be turned upside down and rest upon the lid element, this may be advantageous in that it ensures that the at least partially transparent plate comes into contact with the water inside the container body ensuring a proper photocatalytic effect.

According to another embodiment the ultraviolet light module is configured to be turned off when the lid element is in an open position and the ultra violet light source is configured to be turned on when the lid element is in a closed position. The present embodiment is advantageous in that the ultraviolet light source will not be turned on when the water container is open, this ensures that a user does not stand the risk of being exposed to high energetic ultraviolet light.

According to another embodiment the water container further comprises a switch configured to turn the ultraviolet light source on and off. The present embodiment is advantageous in that the user can choose when the ultraviolet light source is turned on, so as not to use it when there is no need for the purifying effects, for example when there is no water in the container body.

According to another embodiment the water container further comprises an indicator configured to indicate if said ultraviolet light source is on or off. The present embodiment is advantageous in that a user can know whether the light source is on or not, ensuring that the user will not be exposed to any ultraviolet light. Further it allows a user to know for how long the ultraviolet light source has been used and therefore is the water has been purified.

According to another embodiment the second side comprises a coating of metal-oxide nanoparticles. The present embodiment is advantageous in that more metal-oxide nanoparticles lets more radicals be freed during the photocatalytic effect caused by the ultraviolet light which gives a higher rate of interactions with the content of the water. This ensures a faster and more efficient purifying of the water.

According to another embodiment the water container further comprises a second water purifying unit. The present embodiment may have more than one water purifying unit, the second water purifying unit may be similar to the water purifying unit and act in the same way. It may for example be placed on an opposite side of the water container from the water purifying unit. The present embodiment may be advantageous in that more purifying measures may ensure a better purifying effect and a quicker purification process. Further, it may also be advantageous to install a plurality of smaller water purification modules instead of one larger to optimize the container.

According to another embodiment the water container further comprises a power source configured to power the ultraviolet light source. The present embodiment is advantageous in that the ultraviolet light can be powered by a convenient power source. A power source that is both cost effective and environmentally friendly can be chosen. Further, the power source may differ between different embodiments being adapted to certain situations. For example, a hand powered generator may be used for water containers used in areas where there is less sunlight for a solar cell or no access to a power socket for recharging a battery. A battery of solar cell or any other conventional power source may be used in various embodiments.

According to another embodiment an inside of the container body is made of reflective material. The present embodiment is advantageous in that the ultraviolet light will be reflected inside the container body and thusly purify the water more effectively. The light be reflected and therefore have a higher probability of interacting with pollutants in the water. It is further advantageous in that the water will hold a preferred temperature longer, for example if warm water is desired and fills the water container the reflective surface will keep the temperature for longer.

It is noted that other embodiments using all possible combinations of features recited in the above described embodiments may be envisaged. Thus, the present disclosure also relates to all possible combinations of features mentioned herein. Any embodiment described herein may be combinable with other embodiments also described herein, and the present disclosure relates to all combinations of features. In particular, it will be appreciated that the embodiments described above apply to the first and the second aspects of the present disclosure.

BRIEF DESCRIPTION OF THE DRAWINGS

Exemplifying embodiments will now be described in more detail, with reference to the following appended drawing.

DETAILED DESCRIPTION

As illustrated in the figures, the sizes of the elements and regions may be exaggerated for illustrative purposes and, thus, are provided to illustrate the general structures of the embodiments. Like reference numerals refer to like elements throughout.

Exemplifying embodiments will now be described more fully hereinafter with reference to the accompanying drawings, in which currently preferred embodiments are shown. The invention may, however, be embodied in many different forms and should not be construed as limited to the embodiments set forth herein; rather, these embodiments are provided for thoroughness and completeness, and fully convey the scope of the invention to the skilled person.

Figures 1, 2:
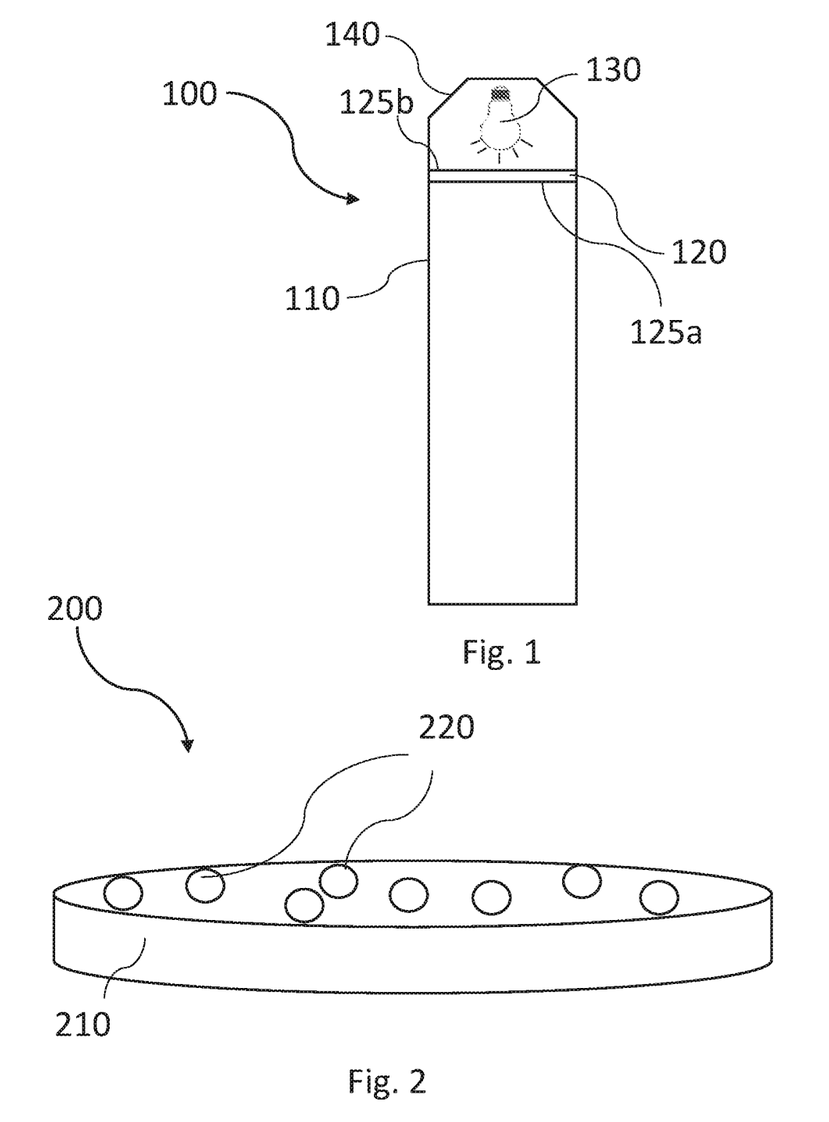
FIG. 1 schematically illustrates an exemplary waiter container in accordance with an embodiment.
FIG. 2 schematically illustrates an exemplary at least partially transparent plate in accordance with the invention.

With reference to FIG. 1 an exemplary water container 100 in accordance with an embodiment is illustrated.

The water container 100 comprises an opening (not shown, see 350b in FIG. 3) configured to receive water. The container 100 further comprises a container body 110 arranged to enclose water filled through the opening. Illustrated is a cross section of the water container 100, the water container 100 may have any convenient shape, for example a cylinder, rectangle or a combination of any shapes. The water container 100 further comprises a water purifying unit configured to purify the water, this water purifying unit comprises an at least partially transparent plate 120 comprising a coating of metal-oxide nanoparticles on a first side 125a facing the container body 110. The first side 125a may be configured to be in contact with the water inside the container body 110. The water purifying unit further comprises an ultraviolet light module 130 configured to radiate toward a second side 125b of the at least partially transparent plate 120 such that light from the ultraviolet light module 130 at least partially passes through the at least partially transparent plate 120. The light radiated from the ultraviolet light module 130 may interact with the metal-oxide nanoparticles on the first side 125a of the at least partially transparent plate 120 and with the water inside the container body 110.

In FIG. 1 the water container 100 further comprises a lid element 140. The ultraviolet light module 130 and the at least partially transparent plate 120 of the water purifying unit are placed in the lid element 140. When the bottle is closed the ultraviolet light module 130 may therefore radiate downwards onto the second side 125b of the at least partially transparent plate 120. Seeing that the plate 120 is at least partially transparent, some ultraviolet light will be transmitted through the plate 120 and in to the container body 110.

The ultraviolet light radiation can therefore purify the water held within the container body 110. Light not transmitted through the plate 120 may interact with the metal-oxide nanoparticles and trigger a photocatalytic effect, which also can act to purify the water. It is however understood that other placements of the ultraviolet light module 130 and the at least partially transparent plate 120 are possible. They may for example be placed in the bottom of the body 110 or on one side of the body 110.

The ultraviolet light module 130 may be a light bulb configured to radiate ultraviolet light radiation. It may for example be configured to radiate ultraviolet light with high energy content, e.g. UVC light. The ultraviolet light module 130 may also be a plurality of light bulbs or light modules placed in any pattern or position configured to radiated towards the at least partially transparent plate 120.

The at least partially transparent plate 120 may be a fully transparent glass plate. It may also be any other suitable material that is at least partially transparent and can allow ultraviolet light to pass through it. The plate 120 may have any thickness or shape suitable for the water container 100. For example, if the water container 100 has a cylindrical shape the plate 120 may have a circular cross-section and fit inside the water container so that all light from the ultraviolet light source 130 needs to pass through or be absorbed by the plate 120.

The container body 110 may be made out of any suitable material. For example, the container body 110 may be made out of metal, a polished metal or made out of glass. If the container body is made out of glass it may allow sunlight to enter through the container body, which may be advantageous since the UV-light of sunlight may interact with the metal-oxide coating.

The metal-oxide nanoparticles may comprise titanium dioxide, $TiO_2$, coated on one side of the at least partially transparent plate 120. The coating may also be placed on more than one side of the plate 120. The metal-oxide may be configured to interact with a portion of the light from the ultraviolet light source 130 in order to create a photocatalytic effect in the water and thereby purifying the water. When ultraviolet light interacts with metal-oxide free radicals can be created and these in turn interact with pollutants in the water which has a purifying effect.

The water container 100 may further comprise a power source configured to power the ultraviolet light source 130. The power source may be any conventional power source, for example the power source may comprise a rechargeable battery, a solar cell or a hand powered generator.

The water container 100 may further comprise a switch configured to turn the ultraviolet light source 130 on and off. The switch may be arranged at any position of the water container 100 so that a user conveniently can turn the ultraviolet light module 130 on and off. The switch may further be configured so that the ultraviolet light module 130 only can be turned on when the water container 100 is closed. This to ensure that a user does not get exposed to any ultraviolet light. The ultraviolet light module 130 may further be configured to be on when the lid element 140 is in a closed position. For example, a sensor overlooking hinges arranged between the lid element 140 and the container body 110 may be configured to control the ultraviolet light module 130. The switch may further be configured to act as a locking unit for the water container 100 ensuring that the water container 100 does not open by accident. The switch may when be turned on and simultaneously lock the water container 100 ensuring that no water can escape and that the ultraviolet light module 130 does not radiate any ultraviolet light outside the water container.

The at least partially transparent plate 120 may be slidably arranged inside the water container 100. This would mean that a user would be able to adjust the position of the at least partially transparent plate 120 by sliding the at least partially transparent plate 120 inside the water container 100 from the outside of the water container 100. This would ensure that the first side 125a of the at least partially transparent plate 120 always could be placed at the surface of the water inside the container body 110 to ensure that the photocatalytic effect works properly, and the water is purified. However, it is understood that other solutions are possible. The water purifying unit may for example be placed in the bottom of the water container 100 ensuring that the water is always in contact with the at least partially transparent plate 120. The water container 100 may also be configured to be turned upside down if the purifying unit is arranged in the lid element 140 to ensure that the water is in contact with the at least partially transparent plate 120.

The water container 100 may be any water container, it may for example be a water bottle for use by a person or user. For example, a water container 100 as disclosed in relation to FIG. 1 may be filled by water from a tap, a stream or any water source that might contain water that needs purifying before drinking.

The inside of the container body 110 may be made out of a reflective material. This can be advantageous since it may allow the ultraviolet light that enters the container body 110 to reflect a number of times within the container body 110. This allows the ultraviolet light to interact with more pollutants in the water held within the container body 110 and thus gives a better purifying effect. The ultraviolet light may also be reflected upwards and interact with the metal-oxide nanoparticles coated on the at least partially transparent plate 120 which can trigger an additional photocatalytic effect.

Further, the inside of the container body 110 may also be coated with metal-oxide nanoparticles, such as $TiO_2$. Such a coating would give the possibility of having a cleaning and purifying effect on the water container 100 itself when the bottle is empty. This would be advantageous in that the water container 100 would be self-cleaning. The container body 110 may be coated similarly as the at least partially transparent plate 120, for example with the same sort of metal-oxide nanoparticles, but it is understood that other metal-oxides are available.

With reference to FIG. 2 an exemplary at least partially transparent plate 200 in accordance with the invention is illustrated.

The at least partially transparent plate 200 comprises a plate body 210 and a coating consisting of metal-oxide nanoparticles 220. The plate body 210 may be of any convenient size so that it fits in a water container as described in relation to FIG. 1. The plate body 210 may for example have a cylindrical or rectangular shape. The size of the plate body 210 may be configured to precisely fit into the body of the water container in FIG. 1 so that it is held in place by friction. It may also be slightly smaller and be fixed via other means of fastening, such as glue, screws or any other convenient fastening structure. It may be advantageous for the plate body 210 to be removable from the water container, this to ensure that the ultraviolet light source can be switched out or attended in case it breaks or fails in any way.

The metal-oxide nanoparticles may comprise of one metal-oxide, for example titanium dioxide. The metal-oxide nanoparticles may also comprise of a mixture of different metal-oxides where at least part of the nanoparticles cause a photocatalytic effect when illuminated by ultraviolet light. The coating of metal-oxide nanoparticles may be applied to one side of the plate body 210, it may also be applied to more than one side of the plate body.

The plate body 210 may comprise of glass, plastic or any other available at least partially transparent material. The plate body 210 may further comprise of a material that allows ultraviolet light frequencies to pass through the plate body 210.

The metal-oxide nanoparticles may be placed evenly distributed on one, or more, sides of the plate body 210. The metal-oxide nanoparticles may also be placed such that the coating goes around the edges and leaves an area in a center of the plate body 210 for allowing UV-light to pass through undisturbed. This may be advantageous in that more UV-light can pass through the plate and clean the water while still remaining the photocatalytic effect from the metal-oxide nanoparticles along the edges. If, for example, the plate body 210 has a circular cross section the area coated with metal-oxide nanoparticles may be the area between two circles with a first radius equal to the radius of the plate body 210 and a second radius smaller than the first radius. The relation between the two radii can differ, as long as an area around the center of the plate body 210 is left free from the coating, or the metal-oxide nanoparticles are placed with enough spacing to allow some UV-light to pass through the plate body 210. It is understood that other geometric shapes of the area left free from coating is possible, if such an area is preferable.

Figure 3:
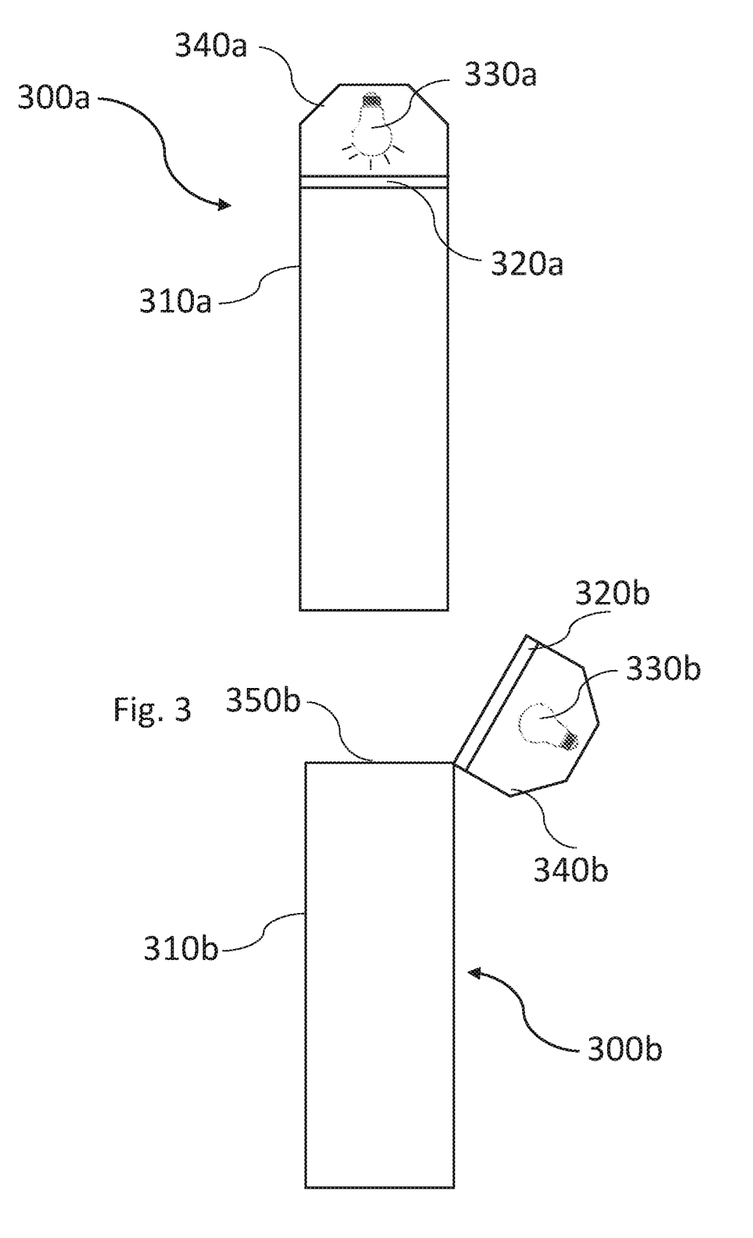
FIG. 3 schematically illustrates an exemplary waiter container in accordance with an embodiment.

With reference to FIG. 3 an exemplary water container 300a, 300b in accordance with an embodiment is illustrated. For a more detailed description of the features and components of the water containers 300a, 300b reference to FIG. 1 is given.

The water container 300a, 300b comprises a lid element 340a, 340b. FIG. 3 illustrates two different positions for the lid element 340a, 340b. The lid element 340a is in a closed position. In the closed position the ultraviolet light module 330a may be allowed to be turned on. The lid element 340b is in an open position. In the open position the ultraviolet light module 330b may not be allowed to be turned on, this to ensure that a user is not expose to ultraviolet light when using the water container 300a, 300b.

While the lid element 340b is in the open position, the water container can also be maintained. For example, if the ultraviolet light module 330a, 330b stops working it can be changed by removing the at least partially transparent plate 320a, 320b if the lid element 340b is in the open position. The ultraviolet light module 330a, 330b may also be changed in other ways, for example by having a hatch at the top of the lid element 340a, 340b that can be opened to reach the ultraviolet light module 330a, 330b.

The water container 300a, 300b comprises an opening 350b configured to receive water to fill the container body 320a, 320b. The opening 350b may be located directly under the lid element 340a, 340b or anywhere on the container body 310.

Figure 4:
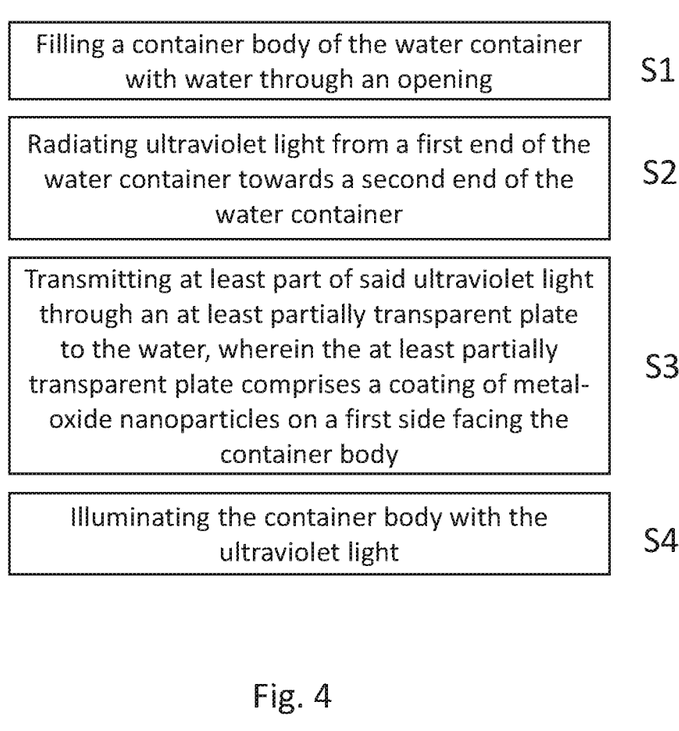
FIG. 4 illustrates an exemplary method for using a waiter container in accordance with an embodiment.

With reference to FIG. 4 an exemplary method for using a waiter container in accordance with an embodiment is illustrated.

In a step S1 a container body of a water container is filled with water. The water may be collected from any water source. For example, contaminated water sources such as certain streams, lakes or the like can be used to the water containers purifying properties. In a second step S2 ultraviolet light is radiated from a first end of the water container towards a second end of the water container. The first side may for example be the top side of the water container, and the light may be radiated towards the bottom part of the water container. However, other positions for the light source is possible. In a third step S3 at least part of the light is transmitted through an at least partially transparent plate toward the container body. The at least partially transparent plate comprises a coating of metal-oxide nanoparticles on a first side facing the container body. In a fourth step S4 the light that has been transmitted through the plate illuminates the container body with ultraviolet light.

The method combines the purifying properties of the ultraviolet light which illuminates the water inside the container body with the photocatalytic effect that occurs when the ultraviolet light illuminates the metal-oxide nanoparticles on the first side of the at least partially transparent plate.

The method may further comprise a step, prior to the second step S2, of closing a lid element comprising at least one of the ultraviolet light source and the at least partially transparent plate. This may be advantageous in that closing the lid before radiating ultraviolet light decreases the risk of the user being exposed to the ultraviolet light.

The method may further comprise a step, sequential to illuminating the container body, of reflecting the ultraviolet light inside the container body on reflective walls of the container body. The ultraviolet light may be reflected to increase the interactions between the ultraviolet light and the pollutants in the water as well as with the coating of metal-oxide on the at least partially transparent plate to increase the photocatalytic effect.

Figure 5:
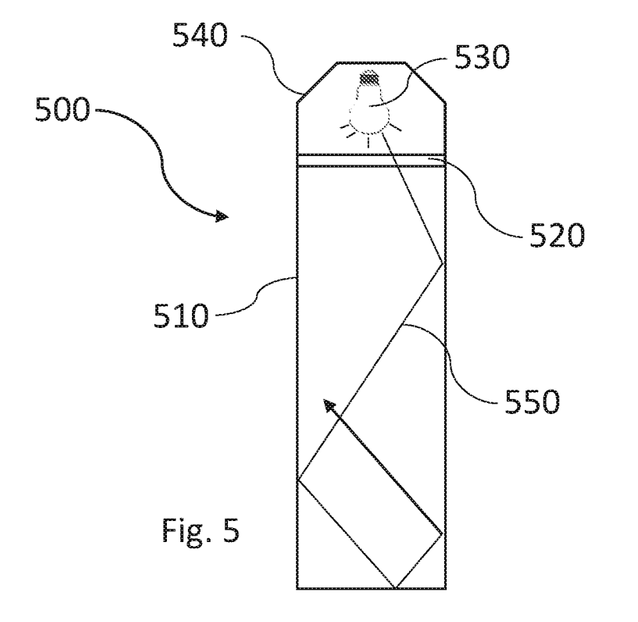
FIG. 5 schematically illustrates an exemplary waiter container in accordance with an embodiment.

With reference to FIG. 5 an exemplary water container 500 in accordance with an embodiment is illustrated. For a detailed explanation of all features presented reference is made to FIG. 1.

The water container 500 illustrated in FIG. 5 comprises a container body 510 which has a reflective inner surface. The reflective inner surface is configured to reflect ultraviolet light from the ultraviolet light source 530. An exemplary light beam 550 is illustrated being reflected a number of times on the inner walls of the container body 510.

The reflective inner surface of the container body may be constructed by any available reflective material, for example a polished metal surface. The reflected light beam 550 may interact with pollutants in the water or be reflected towards the at least partially transparent plate 520 and be absorbed by a metal-oxide nanoparticle causing a photocatalytic effect.

Figure 6:
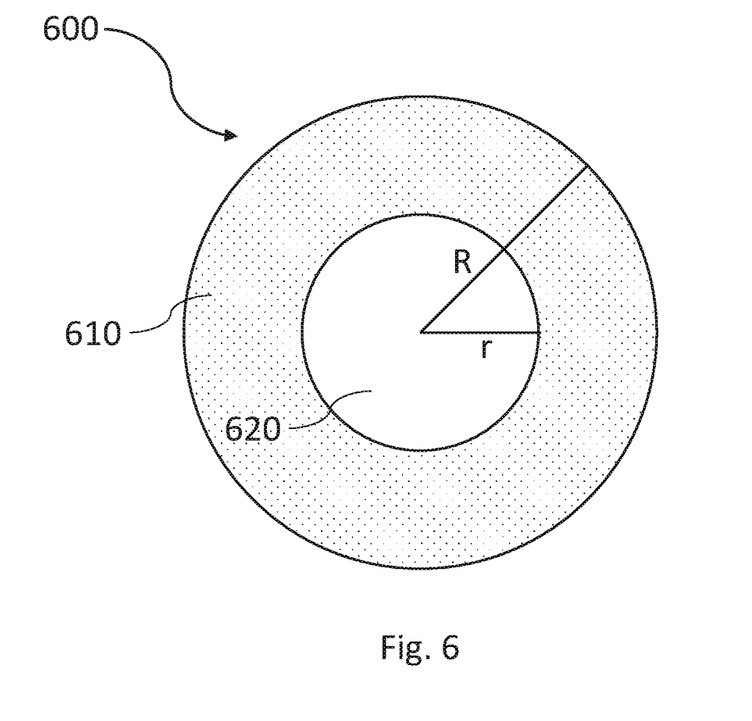
FIG. 6 schematically illustrates an exemplary at least partially transparent plate in accordance with the invention.

With reference to FIG. 6 an exemplary at least partially transparent plate 600 in accordance with the invention is illustrated.

The at least partially transparent plate 600 may have any of the properties explained with relation to any of the other figures, for example FIG. 2.

The at least partially transparent plate 600 may be configured to be used in a water container or bottle in accordance with the invention. The at least partially transparent plate 600 may comprise a coating of metal-oxide nanoparticles in a coated area 610 on a first side. The first side may be arranged toward a waterfilled compartment of a water container or water bottle. The at least partially transparent plate 600 may further comprise a non-coated area 620 configured to allow light to pass through said at least partially transparent plate. The two areas 610, 620 may be determined by two radii r and R respectively stretching from a center point of the first side of the at least partially transparent plate to the edge of the coated area 610 and the edge of the at least partially transparent plate 600. It is understood that other geometries than circular are possible for the at least partially transparent plate 600 and for the coated area 610 and the non-coated area 620.

The embodiment in FIG. 6 may be advantageous in that it allows UV-light to pass through said non-coated area 620 to a water filled container and at the same time allows for the photocatalytic effect to take place via the coated area 610.

Although features and elements are described above in particular combinations, each feature or element can be used alone without the other features and elements or in various combinations with or without other features and elements.

Additionally, variations to the disclosed embodiments can be understood and effected by the skilled person in practicing the claimed invention, from a study of the drawings, the disclosure, and the appended claims. In the claims, the word "comprising" does not exclude other elements, and the indefinite article "a" or "an" does not exclude a plurality. The mere fact that certain features are recited in mutually different dependent claims does not indicate that a combination of these features cannot be used to advantage.

The invention claimed is:

1. A water container for purifying water, said water container comprising;
   an opening configured to receive water;
   a container body arranged to enclose said water; and
   a water purifying unit configured to purify said water,
      wherein said water purifying unit comprises;
      an at least partially transparent plate comprising a coating of metal-oxide nanoparticles on a first side facing said container body, wherein said first side is configured to be in contact with said water; and
      an ultraviolet light module configured to radiate towards a second side of said at least partially transparent plate such that light from said ultraviolet light module at least partially passes through said at least partially transparent plate;
   wherein said at least partially transparent plate is slidably arranged inside said water container.

2. The water container according to claim 1, wherein said coating of metal-oxide nanoparticles comprises Titanium Dioxide, $TiO_2$.

3. The water container according to claim 1, wherein said at least partially transparent plate is a glass plate.

4. The water container according to claim 1, wherein said ultraviolet light module is configured to radiate UVC light.

5. The water container according to claim 1 further comprising a lid element, wherein said water purifying unit is arranged inside said lid element.

6. The water container according to claim 5, wherein said ultraviolet light module is configured to be turned off when said lid element is in an open position and wherein said ultraviolet light module is configured to be turned on when said lid element is in a closed position.

7. The water container according to claim 6 further comprising an indicator configured to indicate if said ultraviolet light module is on or off.

8. The water container according to claim 1 further comprising a switch configured to turn said ultraviolet light module on and off.

9. The water container according to claim 1 wherein said second side comprises a coating of metal-oxide nanoparticles.

10. The water container according to claim 1 wherein said water container further comprises a second water purifying unit.

11. The water container according to claim 1 further comprising a power source configured to power said ultraviolet light module.

12. The water container according to claim 1 wherein an inside of said container body is made of a reflective material.

13. A method for purifying water within a water container according to claim 1, said method comprising;
   filling a container body of said water container with water through an opening;
   radiating ultraviolet light from a first end of said water container towards a second end of said water container;
   transmitting at least part of said ultraviolet light through an at least partially transparent plate towards said container body, wherein said at least partially transparent plate comprises a coating of metal-oxide nanoparticles on a first side facing said container body; and
   illuminating said container body with said ultraviolet light.

14. The method according to claim 13 further comprising, prior to the radiating ultraviolet light, closing a lid element comprising at least one of an ultraviolet light module and said at least partially transparent plate.

* * * * *